United States Patent [19]

Kysela et al.

[11] Patent Number: 4,978,769

[45] Date of Patent: Dec. 18, 1990

[54] PROCESS FOR INTRODUCING FLUORINE ATOMS INTO AROMATIC RINGS BY NUCLEOPHILIC EXCHANGE

[75] Inventors: Ernst Kysela, Bergisch Gladbach; Rudolf Braden, Odenthal, both of Fed. Rep. of Germany

[73] Assignee: Bayer Aktiengesellschaft, Leverkusen, Fed. Rep. of Germany

[21] Appl. No.: 390,577

[22] Filed: Aug. 7, 1989

[30] Foreign Application Priority Data

Aug. 12, 1988 [DE] Fed. Rep. of Germany ....... 3827436

[51] Int. Cl.$^5$ .................... C07C 255/50; C07C 57/72; C07C 22/08; C07C 25/13
[52] U.S. Cl. .................... 558/423; 558/425; 562/864; 568/937; 568/938; 570/147
[58] Field of Search .................... 570/147; 546/345; 558/425, 423; 562/864

[56] References Cited

U.S. PATENT DOCUMENTS

| | | | |
|---|---|---|---|
| 3,453,337 | 7/1969 | Bennett et al. | 570/147 |
| 3,992,432 | 11/1976 | Napier et al. | 260/465.1 |
| 4,071,521 | 1/1978 | Muench | 546/343 |
| 4,229,365 | 10/1980 | Oeser et al. | 558/425 |
| 4,542,221 | 9/1985 | Jones | 546/345 |
| 4,563,529 | 1/1986 | Nishiyama et al. | 546/345 |
| 4,590,315 | 5/1986 | Maul et al. | 558/425 X |
| 4,822,887 | 4/1989 | Little et al. | 546/345 |

FOREIGN PATENT DOCUMENTS

| | | | |
|---|---|---|---|
| 0003344 | 8/1979 | European Pat. Off. | |
| 0120575 | 10/1984 | European Pat. Off. | 570/147 |
| 0192287 | 8/1986 | European Pat. Off. | 546/345 |
| 2938939 | 4/1980 | Fed. Rep. of Germany | |
| 3700779 | 8/1987 | Fed. Rep. of Germany | 546/345 |
| 49-110637 | 6/1973 | Japan | 570/147 |
| 0222463 | 12/1984 | Japan | 558/425 |
| 0072850 | 4/1985 | Japan | 558/425 |
| 0072851 | 4/1985 | Japan | 558/425 |
| 0184057 | 9/1985 | Japan | 558/425 |
| 0228436 | 11/1985 | Japan | 570/147 |
| WO87/04151 | 7/1987 | PCT Int'l Appl. | |
| 2039473 | 8/1980 | United Kingdom | 546/345 |

*Primary Examiner*—Joseph Paul Brust
*Attorney, Agent, or Firm*—Sprung Horn Kramer & Woods

[57] ABSTRACT

Aromatic, ring-fluorinated compounds are particularly advantageously prepared by nucleophilic exchange in the course of reaction wih potassium fluoride in the presence of phase transfer catalysts and, if desired, solvents by carrying out the reaction in the additional presence of metal salts.

6 Claims, No Drawings

PROCESS FOR INTRODUCING FLUORINE ATOMS INTO AROMATIC RINGS BY NUCLEOPHILIC EXCHANGE

The present invention relates to a particularly advantageous process for introducing fluorine atoms into aromatic rings by nucleophilic exchange, in particular by exchange of halogen atoms and/or nitro groups.

A number of processes are known with which it is possible to exchange atom groups or atoms situated on aromatic rings, for example halogen atoms and/or nitro groups, for fluorine atoms. Known processes use potassium fluoride as the fluorinating agent, which is generally employed in the presence of a high-boiling, inert solvent and, if appropriate, in the presence of phase transfer catalysts (see, for example, DE-OS (German Published Specification) No. 2,938,939 or EP-OS (European Published Specification) No. 0,003,344). Suitable phase transfer catalysts are, for example, quaternary ammonium salts, quaternary phosphonium salts and crown ethers. The relatively high temperatures still to be used are disadvantageous, which has negative influences on the energy requirement, corrosion, the possibility of decomposition reactions and the lifetime of the phase transfer catalysts.

A process for the preparation of aromatic, ring-fluorinated compounds by nucleophilic exchange with potassium fluoride in the presence of phase transfer catalysts and, if desired, solvents has now been found, which is characterized in that the reaction is carried out in the additional presence of metal salts.

For the process according to the invention, possible salts are, for example, those of metals of main groups 3 to 5 of the periodic table of the elements and those of sub-group elements. Halides and sulphates are preferred, particularly preferably chlorides. Possible examples are: chromium salts such as $CrCl_3 \times 6H_2O$, iron salts such as $FeCl_3$, cobalt salts such as $CoCl_2 \times 6H_2O$, nickel salts such as $NiCl_2 \times 6H_2O$, copper salts such as $CuSO_4$, aluminium salts such as $AlCl_3$, zinc salts such as $ZnCl_2$ and antimony salts such as $SbCl_3$.

The metal salts can be employed in various proportions. For example, 0.1 to 10 moles of metal salt can be employed relative to 1 mole of phase transfer catalyst employed. Preferably this amount is 0.2 to 5 moles, in particular 0.25 to 1 mole.

During the fluorination reaction, the phase transfer catalyst employed in each case and the metal salt employed in each case can be present wholly or partially as complexes formed in situ, for example as complexes of the type

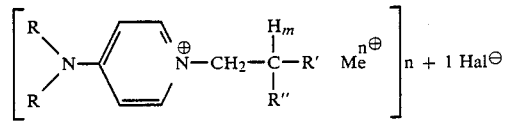

where
R independently of one another in each case denotes a one-bonded organic radical, for example in each case $C_1$- to $C_{10}$-alkyl, and
R' and R" in each case denotes a $C_1$- to $C_{10}$-alkyl group or together with the C atom situated in between denotes a saturated carbocyclic ring having a total of 5 to 6 C atoms, where m in each case then represents 1 or where R' and R" together with the C atom situated in between denotes a carbocyclic aromatic ring having 6 C atoms, where m then represents zero,
Me denotes a metal ion having n positive charges and
Hal denotes halogen.

The phase transfer catalyst employed in each case and/or the metal salt employed in each case can also be introduced wholly or partially into the reaction mixture in the form of complexes.

Possible phase transfer catalysts are, for example, quaternary nitrogen compounds, quaternary phosphorus compounds, pyridinium salts and crown ethers. The 3 first-mentioned catalyst types can correspond, for example, to the formulae

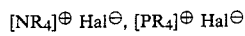

or

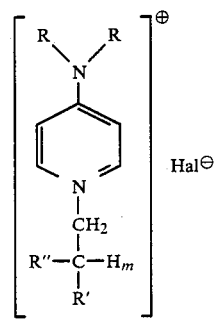

where
R, R', R", m and Hal have the abovementioned meaning.

Preferably, quaternary nitrogen compounds or pyridinium salts are used, for example methyltrioctylammonium chloride, tetrabutyl-ammonium chloride, tetrabutyl-ammonium bromide, tetraethylammonium chloride, triethylbenzyl-ammonium chloride, dimethylbenzyl-phenyl-ammonium chloride, dimethyldodecylbenzyl-ammonium chloride, tetraphenyl-phosphonium bromide, triphenyl-benzyl-phosphonium bromide, N',N'-dimethylamino-N-benzyl-pyridinium chloride or N',N'-dimethylamino-N-2-dimethylpropylpyridinium chloride. When using crown ethers, the ether 18 crown 6 is preferred.

The phase transfer catalysts can be employed, for example, in amounts from 0.1 to 20 mol-%, relative to the educt. Preferably, this amount is 0.5 to 5 mol-%.

The process according to the invention does not always have to be carried out in the presence of solvents. Instead of solvents, an excess of the aromatic compound to be fluorinated may also be employed. Frequently, good results are obtained even when employing nitroaromatics without solvents. In spite of this, it is generally preferred to use solvents.

Solvents which can be used are virtually all aprotic, dipolar solvents which have a sufficiently high boiling point and are sufficiently inert under the reaction conditions, for example dimethyl sulphoxide, N-methylpyrrolidone, tetramethylene sulphone, benzonitrile, nitrobenzene, dimethylacetamide, ethylene glycol dimethyl ether and diglyme.

The reaction temperatures for the process according to the invention may be, for example, in the range 100° to 250° C. Preferably, the reaction is carried out in the range 130° to 180° C.

The potassium fluoride can be employed in various amounts. In general, the stoichiometrically required amount or more is employed. Large excesses are not critical, but are economically inefficient. Preferably, 1.1 to 2 moles of potassium fluoride are therefore employed per mole of fluorine atoms to be introduced.

Aromatics having various leaving groups can be employed as the educt in the process according to the invention.

Preferably, the leaving groups intended to be exchanged with fluorine are activated by means of one or more further -I and/or -M substituents, for example by halogen, CN, CO-halogen, $SO_2$-halogen or $CF_3$. Preferred educts contain halogen and/or nitro substituents as leaving groups, for example 1 to 3 chlorine atoms bonded to the aromatic ring and/or 1 to 2 nitro groups bonded to the aromatic ring. Examples of educts which may be mentioned are:

3,4-dichloro-nitrobenzene, 2,4-dichloro-nitrobenzene, 2,4-dichloro-5-fluoro-benzoyl chloride, 3,4-dichloro-benzoyl chloride, 2,6-dichloro-benzonitrile, 2-nitro-6-chlorobenzonitrile, 2-trifluoromethyl-4-nitrochlorobenzene, pentachlorobenzotrifluoride, 4-trifluoromethyl-tetrachlorobenzoyl chloride and 3,4,5-trichloro-benzotrifluoride.

Preferably, halogen atoms and/or nitro groups on the aromatic ring are exchanged for fluorine atoms using the process according to the invention. In particular, a number of halogen atoms and/or nitro groups of this type, preferably up to 5 chlorine atoms and/or 1 to 2 nitro groups can also be exchanged for fluorine.

Possible vessel materials for carrying out the reaction according to the invention are, for example, glass, steel alloyed with nickel and/or chromium and perfluorinated olefin polymers. Perfluorinated olefin polymers, for example polytetrafluoroethylene, are preferred. When using metal vessels, the possibility of metal salts derived from vessel materials passing into the reaction mixture to a small extent cannot be excluded. In certain circumstances (with a useful type and amount of the metal salts formed), this effect may be desired.

All components of the reaction mixture are preferably employed in dry or substantially anhydrous form. If necessary, small amounts of water present in the reaction mixture can be removed by distilling off (if desired together with a small proportion of the solvent used) or by azeotropic distillation using an entrainer.

The mixture present after the reaction can be worked up in different ways, depending on the proportions present therein.

In the presence of a solvent which has a higher boiling point than the aromatic, ring-fluorinated product, the mixture can be distilled until the solvent passes over and, if desired, the solvent can be (substantially) recovered from the salt-containing residue which is still present by distilling or filtering. In the presence of a solvent which has a lower boiling point than the aromatic ring-fluorinated product, the solvent can first be removed by distillation and the product can then be recovered by further distillation or extraction. In the presence of a solvent which can only be separated by distillation from the aromatic ring-fluorinated product with difficulty, the product can be recovered either by extraction or by introducing the optionally filtered reaction mixture into water and separating off the organic phase. In the absence of an independent solvent, aromatic, ring-fluorinated product and unreacted starting compound can be separated from one another by distillation. All distillations mentioned are preferably carried out in vacuo.

The process according to the invention has the surprising advantage that it can be carried out at a lower temperature with a given reaction time or in a shorter time with a given temperature. Compared to known processes, this means a lowering of the energy requirement, the corrosion and the possibility of decomposition reactions and a lengthening of the lifetime of the phase transfer catalysts.

Which combinations of a metal salt with a phase transfer catalyst and, if desired, a solvent yields optimum results can be determined, if desired, by a simple series of experiments. For different aromatic chlorine and/or nitro compounds to be fluorinated, in each case another qualitative and/or quantitative combination of metal salt, phase transfer catalyst and, if desired, solvent can produce an optimum result.

EXAMPLE 1

A mixture of 87 g (1.5 mol) of potassium fluoride and 250 g of tetramethylene sulphone in a glass reaction vessel was subjected to incipient distillation for the removal of water until 25 g of tetramethylene sulphone had passed over. 192 g of 3,4-dichloro-nitrobenzene, 10 g (0.025 mol) of methyl -trioctyl-ammonium chloride and 1.65 g (0.0125 mol) of $AlCl_3$ were then added and the was 97% (determined by gas chromatography). The reaction mixture was then worked up by distillation. 149 g of 3-chloro-4-fluoro-nitrobenzene having a boiling point of 92°–93° C. at 10 mbar were obtained. This corresponds to a yield of 85% of theory.

EXAMPLES 2 TO 16

The procedure was as in Example 1, but the type of metal salt, the type of phase transfer catalyst and the type of solvent was varied and, for comparison, examples without metal salt addition and without addition of a phase transfer catalyst also carried out. Water-containing metal salts were added to the mixture of potassium fluoride and tetramethylene sulphone before incipient distillation in order to remove the entrained water before the beginning of the reaction.

The details are evident from Table 1. In Table 1, A in the column "Phase transfer catalyst" represents methyltrioctyl-ammonium chloride, B represents tetraethylammonium chloride, C represents tetrabutylammonium bromide, D represents N',N'-dimethylamino-N-2-ethylhexyl-pyridinium chloride and E represents N',N'-dimethylamino-N-benzyl-pyridinium chloride, TMS in the column "Solvent" represents tetramethylene sulphone and n.w. in the column "Yield . . . " denotes not worked up.

If no solvent was employed, for working up the mixture was diluted with 50 ml of methylene chloride, filtered, the solid residue washed with 25 ml of methylene chloride and the combined filtrates distilled.

TABLE 1

| Example No. | Metal salt | Phase transfer catalyst | Solvent | Achieved conversion of y % after x hours x | Achieved conversion of y % after x hours y | Yield of 3-chloro-4-fluoronitro-benzene [% of theory] | Remarks |
|---|---|---|---|---|---|---|---|
| 2 | $CrCl_3 \times 6 H_2O$ | A | TMS | 6 | 97 | 86 | |
| 3 | $CoCl_2 \times 6 H_2O$ | A | TMS | 6 | 97 | 85 | |
| 4 | $FeCl_3$ | A | TMS | 6 | 97 | 82 | |
| 5 | $CrF_3 \times 4 H_2O$ | A | TMS | 8 | 97 | 80 | |
| 6 | — | A | TMS | 10 | 97 | 81 | For comparison |
| 7 | $FeCl_3$ | — | TMS | 10 | 46 | n.w. | For comparison |
| 8 | $AlCl_3$ | B | TMS | 6 | 98 | 85 | |
| 9 | — | B | TMS | 10 | 94 | 81 | For comparison |
| 10 | $FeCl_3$ | C | TMS | 6 | 98 | 83 | |
| 11 | — | C | TMS | 10 | 96 | 80 | For comparison |
| 12 | $CrCl_3 \times 6 H_2O$ | D | — | 4 | 99 | 87 | |
| 13 | $FeCl_3$ | D | — | 4 | 98 | 85 | |
| 14 | — | D | — | 12 | 96 | 87 | For comparison |
| 15 | $FeCl_3$ | E | — | 4 | 95 | 81 | |
| 16 | — | E | — | 8 | 90 | n.w. | For comparison |

EXAMPLES 17 TO 20

The procedure was as in Example 1, but a corresponding amount of 4-chloro-nitrobenzene was employed instead of 3,4-dichloro-nitrobenzene, a corresponding amount of N',N'-dimethylamino-N-2-ethyl-hexyl-pyridinium chloride was employed instead of methyl-trioctyl-ammonium chloride and 4-fluoro-nitrobenzene was obtained instead of 3-chloro-4-fluoronitrobenzene. In addition, the phase transfer catalyst was varied (Example 19) and examples were carried out for comparison without addition of metal salt (Examples 18 and 20).

Details are evident from Table 2, in which the same abbreviations are used as in Table 1.

TABLE 2

| Example No. | Metal salt | Phase transfer catalyst | Solvent | Achieved conversion of y % after x hours x | Achieved conversion of y % after x hours y | Yield of 4-fluoro-nitrobenzene [% of theory] | Remarks |
|---|---|---|---|---|---|---|---|
| 17 | $CrCl_3 \times 6 H_2O$ | D | TMS | 6 | 97 | 92 | |
| 18 | — | D | TMS | 12 | 93 | 91 | For comparison |
| 19 | $CrCl_3 \times 6 H_2O$ | E | TMS | 8 | 99 | 85 | |
| 20 | — | E | TMS | 12 | 97 | 83 | For comparison |

EXAMPLES 21 TO 23

192 g (1 mol) of 2,4-dichloronitrobenzene and 87 g (1.5 mol) of potassium fluoride were heated for 8 hours at 180° C. with the addition of 0.025 mol of the compound indicated in each case. The conversion was then determined by gas chromatography and the composition of the crude distillate was determined after working up by distillation.

The details are evident from Table 3. The meaning of E is as indicated in the explanation of Table 1, E' denotes the corresponding pyridinium cation.

TABLE 3

| Example No. | Compound employed | After 8 hours a = % by weight of starting compound b = % by weight of monofluoro compound c = % by weight of difluoro compound | Yield of difluoro compound [% of theory] |
|---|---|---|---|
| 21+ | E | a 34.6 b 45.2 c 16.9 | 12 |
| 22 | $[E'_2Co^{2+}] Cl_4^-$ | a 21.4 b 49.0 c 30.0 | 25 |
| 23 | $[E'Fe^{3+}]Cl_4^-$ | a 22.2 b 48.0 c 29.0 | 24 |

+For comparison

EXAMPLES 24 TO 28

157 g (1 mol) of 4-chloro-nitrobenzene, 87 g (1.5 mol) of potassium fluoride, 150 g of tetramethylene sulphone, 6.77 g (0.025 mol) of N,N'-dimethylamino-N-2-ethyl-hexyl-pyridinium chloride (=D) and varying amounts of $CrCl_3 \times 6H_2O$ were combined and heated for 16 hours at 170° C. The conversion was then determined by gas chromatography. The details are evident from Table 4.

TABLE 4

| Example No. | Molar ratio D:$CrCl_3 \times 6H_2O$ | Conversion after 16 hours [%] |
|---|---|---|
| 24 | 1:0.1 | 84 |
| 25 | 1:0.5 | 98 (after only 12 hours) |
| 26 | 1:1 | 98 |

TABLE 4-continued

| Example No. | Molar ratio D:CrCl₃ × 6H₂O | Conversion after 16 hours [%] |
|---|---|---|
| 27 | 1:2 | 97 |
| 28 | 1:2 | 90.7 |

EXAMPLES 29 TO 33

172 g (1 mol) of 2,6-dichlorobenzonitrile, 174 g (3 mol) of potassium fluoride, 0.025 mol of phase transfer catalyst (PTC) and 0.0125 mol of metal salt are heated for 4 hours at 170° C. together with 450 g of solvent. The composition of the crude distillate is then determined by gas chromatography after working up by distillation. The details are evident from Table 5. In the column "Solvent", TMS represents tetramethylene sulphone, BN represents benzonitrile and NB represents nitrobenzene. In the column PTC, the abbreviations used have the meaning indicated in the explanation of Table 1.

TABLE 5

| Example No. | Solvent | PTC | Metal salt | Content after 4 h a = starting compound b = monofluoro compound c = difluoro compound [% by weight] |
|---|---|---|---|---|
| 29 | TMS | E | CrCl₃ × 6 H₂O | a 28<br>b 48<br>c 23 |
| 30+ | BN | E | — | a 47<br>b 48 |
| 31 | BN | E | CrCl₃ × 6 H₂O | a 13<br>b 49<br>c 33 |
| 32+ | NB | D | — | a 72<br>b 20<br>c 7 |
| 33 | NB | D | FeCl₃ | a 30<br>b 58<br>c 12 |

+For comparison

EXAMPLES 34 AND 35

172 g (1 mol) of 2,6-dichloro-benzonitrile, 174 g (3 mol) of potassium fluoride, 450 g of dimethyl, sulphoxide and 0.025 mol of tetraphenylphosphonium bromide were heated for 4 hours at 150° C., once in the absence of FeCl³ (Example 34) and once in the presence of 0.0125 mol of FeCl² (Example 35). The composition of the crude distillate was then determined by gas chromatography after working up by distillation. The details are indicated in Table 6.

TABLE 6

| Example No. | Content after 4 hours b = monofluoro compound c = difluoro compound [% by weight] |
|---|---|
| 34(+) | b 42<br>c 58 |
| 35 | b 24 |

TABLE 6-continued

| Example No. | Content after 4 hours b = monofluoro compound c = difluoro compound [% by weight] |
|---|---|
| | c 75 |

(+)for comparison

We claim:

1. In the preparation of an aromatic ring-fluorinated compound by nucleophilic exchange between an educt and potassium fluoride in the presence of a phase transfer catalyst, the improvement wherein the educt is selected from the group consisting of 3,4-dichloro-nitrobenzene, 2,4-dichloro-nitrobenzene 2,4-dichloro-5-fluoro-benzoyl chloride, 3,4-dichloro-benzoyl chloride, 2,6-dichloro-benzonitrile, 2-nitro-6-chlorobenzonitrile, 2-trifluoromethyl-4-nitrochlorobenzene, pentachlorobenzotrifluoride, 4-trifluoromethyl-tetrachlorobenzoyl chloride and 3,4,5-trichlorobenzotrifluoride, the phase transfer catalyst is a quaternary nitrogen compound, a quaternary phosphorus compound, a pyridinium salt or a crown ether, and the reaction is effected in the additional presence of a salt of a metal of main groups 3 to 5 of the periodic table of the elements and of sub-group elements, the reaction is effected at from about 100° to 250° C., about 0.1 to 10 moles of the metal salt being present per mole of phase transfer catalyst, and about 0.1 to 20 mole % of the phase transfer catalyst being present based on the educt.

2. A process according to claim 1, in which dimethyl sulphoxide, N-methylpyrrolidone, tetramethylene sulphone, benzonitrile, nitrobenzene, dimethylacetamide, ethylene glycol demethyl ether or diglyme are employed as solvents.

3. A process according to claim 1, in which 1.1 to 2 moles of potassium fluoride are employed per mole of fluorine atoms to be introduced.

4. A process according to claim 1, in which all components of the reaction mixture are employed in dry form.

5. A process according to claim 1, in which small amounts of water present in the reaction mixture are removed by distilling off.

6. A process according to claim 1, in which the metal of the salt of a metal of main groups 3 to 5 of the periodic table is selected from the group consisting of chromium, iron, cobalt, nickel, copper, aluminum, zinc and antimony.

* * * * *